United States Patent [19]

McPherson et al.

[11] Patent Number: 5,322,938
[45] Date of Patent: Jun. 21, 1994

[54] DNA SEQUENCE FOR ENHANCING THE EFFICIENCY OF TRANSCRIPTION

[75] Inventors: Joan C. McPherson, Vancouver; Robert Kay, West Vancouver, both of Canada

[73] Assignee: Monsanto COmpany, St. Louis, Mo.

[21] Appl. No.: 977,600

[22] Filed: Nov. 17, 1992

Related U.S. Application Data

[63] Continuation of Ser. No. 395,155, Aug. 17, 1989, Pat. No. 5,164,316, which is a continuation of Ser. No. 147,887, Jan. 25, 1988, abandoned, which is a continuation-in-part of Ser. No. 2,780, Jan. 13, 1987, abandoned.

[51] Int. Cl.$^5$ .................... C07H 21/04; C12N 15/67; C12N 15/82
[52] U.S. Cl. ................................. 536/24.1; 435/69.1; 435/70.1; 435/172.3; 435/240.4; 435/320.1; 800/205; 935/35; 935/36
[58] Field of Search ................. 435/172.3, 320.1, 69.1, 435/70.1, 240.4; 800/205; 935/35, 36; 536/24.1

[56] References Cited

PUBLICATIONS

Odell et al 1985 Nature 313:810–812.
Schaffner 1985 In Eukaryotic Transcription: The role of cis-and trans-acting elements in initiation; Gluzman (ed); (publ. Cold Spring Harbor Laboratory, Cold Sping, Harbor N.Y.) pp. 1–18.
Zenke et al 1986 EMBO J 5(2):387–397.
Kumar et al 1986 Proc Natl Acad Sci 83:3199–3203.

*Primary Examiner*—Patricia R. Moody
*Attorney, Agent, or Firm*—Grace L. Bonner; Dennis R. Hoerner; Richard H. Shear

[57] ABSTRACT

Novel transcription initiation regions that provide for enhanced transcription or a DNA sequence, particularly a plant sequence, are provided.

6 Claims, 4 Drawing Sheets

DNA SEQUENCE FOR ENHANCING THE EFFICIENCY OF TRANSCRIPTION

CROSS REFERENCE TO RELATED APPLICATIONS

This application is a continuation of U.S. Ser. No. 07/395,155, filed Aug. 17, 1989, now U.S. Pat. No. 5,164,316, which is a continuation of U.S. Ser. No. 07/147,887, filed Jan. 25, 1988, now abandoned, which is a continuation-in-part of U.S. Ser. No. 07/002,780, filed Jan. 13, 1987, now abandoned.

TECHNICAL FIELD

The present invention relates to DNA constructs that permit variation in enhancement of transcription initiation rate, particularly in plants.

BACKGROUND OF THE INVENTION

The ability to manipulate gene expression would provide a means of producing new characteristics in transformed plants. There are many situations for which high or increased levels of gene expression may be required; for example the production of important proteins for agronomical or commercial purposes, or the regulation of endogenous gene expression by competing levels of anti-sense RNA. The enhancement of transcription from promoters would facilitate these possibilities. Promoters vary in their transcription initiation rate and/or efficiency. Besides the transcription levels from a promoter other factors such as regulated or enhanced transcription should be considered. It is therefore of interest to provide DNA constructs which provide flexibility in the levels of expression obtained and under the appropriate conditions in which they are required to be effective.

DESCRIPTION OF THE RELEVANT LITERATURE

Barton et al., *Cell* (1983) 32:1033-1043, Caplan et al., *Science* (1983) 222:815-821, Nester et al., *Ann. Rev. Plant Physiol.* (1984) 35:387-413, and Fraley et al., *Biotechnology* (1985) 3:629-635 describe the genetic transformation of dicotyledonous plants by the transfer of DNA from *Agrobacterium tumefaciens* (*A. tumefaciens*) through the mediation of modified Ti plasmids. Odell et al., *Nature* (1985) 313:810-812 describe that the cauliflower mosaic virus (CaMV) 35S promoter is constitutively active in several different species of plants. Bevan et al., *EMBO J.* (1985) 4:1921-1926 and Morelli et al., *Nature* (1985) 315:200-204 describe that the CaMV 35S promoter is transcribed at a relatively high rate as evidenced by a ten-fold increase in transcription products in comparison to the NOS promoter. Abel et al., *Science* (1986) 232:738-743, Bevan et al., *EMBO J.* (1985) 4:1921-1926, Morelli et al., *Nature* (1985) 315:200-204, and Shah et al., *Science* (1986) 233:478-481 describe that the 35S promoter is moderately strong and constitutively active, and so has been used to express a number of foreign genes in transgenic plants. Odell et al., supra, describe that correct initiation of transcription from the 35S promoter is dependent on proximal sequences which include a TATA element, while the rate of transcription is determined by sequences that are dispersed over 300 bp of upstream DNA. Simpson et al., *Nature* (1986) 323:551-554 describe an enhancer region. (Sequences which activate transcription are termed enhancers.)

SUMMARY OF THE INVENTION

The present invention provides a novel transcription initiation region comprising an enhancer domain and, under the enhancing control of the enhancer domain, a transcription initiation domain. The enhancer domain comprises a plurality of the repetitive units of a natural enhancer spaced in substantially the same way as a natural enhancer. In the absence of a heterologous transcription initiation domain, the enhancer domain has at least one more repetitive unit than the natural enhancer. The transcription initiation domain or promoter comprises an RNA polymerase binding site and an mRNA initiation site. The transcription initiation regions of the present invention provide for an enhanced transcription efficiency as compared to the promoter in the absence of the enhancer domain.

DNA constructs are also provided comprising a transcription initiation region and a DNA sequence, which may be the RNA coded sequences of a gene or RNA sequences of opposite orientation in relation to the wild-type transcription initiation domain (anti-sense sequence), particularly a plant sequence. The constructs provide for an enhanced efficiency of transcription of the RNA coded regions.

Figure 1:
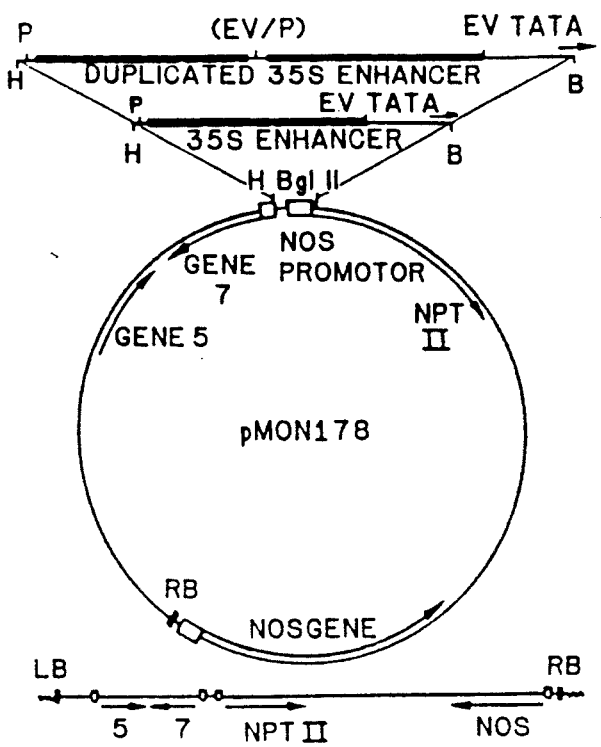
FIG. 1 illustrates diagrammatically the organization of genes in intermediate vectors pCKR1 and pCKR2 and transgenic plants. Abbreviations used in the Figure are B, BamHI; EV, EcoRV; H, HindIII; P, PstI; (EV/P), fusion of EcoRV and PstI sites.

Abbreviations used in FIGS. 2-5 include, for restriction sites Eco - Eco RI; Hind or H - Hind III; Pst or P - Pst I; Xba - Xba I; Barn - Barn HI; Cla - ClaI; Sma - SmaI; Xho - XhoI; Kpn - KpnI; Sph - SphI; Ssp - SspI; N - NheI; A - AluI; EV - EcoRV;

For other sequences: G7 - gene 7; Po - promoter; Sp$^r$ - streptomycin resistance; NPT - neomycin phosphotransferase; Ca2 promoter - Cauliflower mosaic virus 35S promoter with upstream enhancer duplication; nos - nopaline synthase.

DESCRIPTION OF THE SPECIFIC EMBODIMENTS

The present invention provides a novel transcription initiation region, particularly chimaeric or heterologous region, comprising an enhancer domain and a transcription initiation domain under the enhancing control of the enhancer domain. The transcription initiation regions of the present invention are useful in enhancing the transcription efficiency which may result in enhanced transcription of DNA sequences under control of the transcription initiation region. Of particular interest is enhanced transcription of inserted gene sequences which may be of the same genetic origin as the host or of foreign origin, either the naturally occurring sequences (in both sense and antisense orientations) or synthetically prepared sequences.

The subject enhancer domains comprise a plurality of the repetitive units of a natural enhancer spaced in substantially the same way as the natural enhancer, including the natural or wild-type enhancer. The enhancer domain comprises at least the same number of the repetitive units as the natural enhancer and need be no more than the number of repeated elements for the optimal expression required, usually not more than about three times the number of the repetitive units of the natural enhancer. When the transcription initiation region does not include a heterologous transcription initiation domain (promoter), the enhancer domain has at least one more repetitive unit than the natural enhancer. A natural enhancer comprises a DNA sequence which in its native environment is upstream from and within about 600 bp of a promoter. Taking the initial nucleotide of the mRNA as 0, the sequence containing an enhancer is from about −50 to about −1000 bp, usually from about −50 to −950 bp, generally comprising about −100 to −800 bp.

The subject DNA enhancer sequences contain repetitive units comprising short sequences of from about 4 to about 16 bp, including four unit, seven unit and ten unit repeats, which are repeated within the sequence comprising the enhancer. The repeat will usually include at least the unit GTGG (CACC), although in some instances one of the G's may be replaced by an A, particularly the second G. Exemplary of such repetitive units is the sequence GTGG (or complementary sequence CCAC), $$GTGG_{TTT}^{AAA}, \text{ and } GTGTGG_{TTT}^{AAA}G,$$

the former two being repeated several times within the upstream sequence of the CaMV 35S promoter region. The repeats may be imperfect, having a specific core and some degree of variability in the surrounding sequence. The repeats may be used in combination or as independent repeat sequences, that is the same or different sequences may be repeated.

By similarly spaced to a natural enhancer, it is meant that the number of nucleotides between the repetitive units is substantially the same as in the natural enhancer. This will generally be at least about 4 and not more than 100 nt. Usually the repetitive units will be separated by not more than the largest number of nucleotides separating the repetitive units in the natural enhancer and not fewer than the smallest number of nucleotides separating the repetitive units in the natural enhancer. More usually, the repetitive units in the enhancer domain will have an average spacing which is within about 16 bp, more usually within about 4 bp, of the average spacing of the repetitive units in the natural enhancer. Conveniently, the spacers between repetitive units may be the same as the wild-type enhancer, recreating the wild-type enhancer and extending the wild-type enhancer with a fragment of or a complete enhancer region. The spacer nucleotides may be the same or different from the wild-type spacer nucleotides and may be in the same or different order from the wild-type spacer order.

For the most part the enhancer domain will have at least about 4, usually at least about 6, and preferably at least about 8 repeats of the 4 bp sequence, and a total of at least about 3, usually at least about 4, of the 7 and 10 bp sequences. Generally, there will be from about 4 to 100 bp separating the repeat sequences. Of course, since GTGG is present in the longer sequences, in referring to the number of repeat sequences, the requirements for GTGG should not be read into the requirements for the longer sequences.

The enhancer domain will usually be at least about 25 bp, more usually at least about 30 bp, generally at least about 50 bp and not more than about 1 kbp, usually not more than about 700 bp, frequently not more than about 600 bp.

The enhancer sequence will come from sources which function efficiently in eukaryotes, particularly of higher multi cellular orders of eukaryotes, more particularly plants and animals, usually plants. Usually the enhancer will be of vital or (higher) eukaryotic origin. The enhancer may be used in the same or different kingdom, genus or species from which it is derived or in which it naturally functions.

Many viral, plant and animal enhancers contain sets of repeated sequence elements (repetitive units) (Shaffner, *Eukaryotic Transcription: the Role of cis- and trans-acting Elements in Initiation* (1985) ed. Y. Gluzman, 1–18). For example, several short (4 to 7 bp) sequences are repeated within the upstream sequences of the CaMV 35S promoter. Among these, the sequences GTGG (and its complement CCAC) and $$GTGG_{TTT}^{AAA}$$

are distinguished by being selectively localized adjacent to and upstream from the two promoter regions of the CaMV genome. The 270 bp of DNA upstream from the TATA element of the 35S promoter contains ten copies of these sequences and the 19S promoter has four copies dispersed over 150 bp of DNA immediately upstream from its TATA element. The remaining 7600 bp in the CaMV genome contains only 26 GTGG sequences (Franck et al., *Cell* (1980) 21:285–294).

GTGG sequences are concentrated upstream from or within the promoter regions of many plant genes (Coruzzi et al., *EMBO J.* (1984) 3:1671–1679, Dean et al., *EMBO J.* (1985) 4:3055–3061, Doyle et al., *J. Biol. Chem.* (1986) 261:9228–9238, Fluhr et al., *Science* (1986) 232:1106–1112, Herrera-Estrella et al., *Nature* (1984) 310:115–120, and Sommer and Saedler, *Mol Gen. Genet.* (1986) 202:429–434). A subset of these sequences have attracted attention (Odell et al. (1985) supra, Coruzzi et al. (1984) supra, Dean et al. (1985) supra, Doyle et al. (1986) supra, Fluhr et al. (1986) supra, and Kaulen et al., *EMBO J.* (1986) 5:1- ) because they resemble the sequence $$GTGTGG_{TTT}^{AAA}G,$$

which is common to many of the enhancers associated with vital and animal genes (Weiher et al., *Science* (1983) 219:626–631). Extensive upstream sequences of some light-regulated plant promoters which contain GTGG sequences can activate transcription when positioned in either orientation upstream of a heterologous promoter Fluhr et al. (1986), supra, and Timko et al., *Nature* (1985) 318:579–582). However, such an upstream promoter region excised from a ribulose bisphosphate carboxylase small subunit gene had no significant enhancing effect when placed downstream of a heterologous promoter (Timko et al. (1985) supra). Similarly an upstream element of the light harvesting protein gene (lhcp) gene gave no enhanced expression when placed 3' to the expressed sequences (Simpson et al. *Nature* (1986) 323: 551-554).

An enhancer domain is cis-acting and desirably is located within about 5000 bp, usually about 2000 bp, more usually adjacent to or within about 1000 bp of a transcription initiation domain to be enhanced. The enhancer may be in either orientation, e.g.,

$$5'\text{-(GT)}_a\text{GTGG}(\tfrac{AAA}{TTT})_b G_a\text{-}3',$$

with respect to the transcription initiation domain and can be located upstream or downstream in relation to the promoter it enhances, usually upstream. (a is 0 or 1, and b is 0 or 1.)

An enhancer domain of the present invention finds use with a wide variety of initiation domains, including promoters that are naturally found under the control of the enhancer, i.e., in a cis position (adjacent and homologous) and those not normally associated with the particular promotor (i.e., heterologous).

The enhancer domain and transcription initiation domain may be from the same or different kingdom, family or species or a pathogen which functions in the cell source of the initiation region (promoter). Species of interest include prokaryotes and eukaryotes, such as bacteria, plants, insects, mammals, etc. Combinations may include enhancer domains from a virus with a transcription inititiation region of a structural gene of a host for the virus; an enhancer domain from one species with a gene (structural gene and promoter) from a different species of the same or different family; etc.

The invention also contemplates DNA constructs comprising a subject transcription initiation region and, under the control of the transcription initiation region, a DNA sequence to be transcribed. The DNA sequence may comprise a natural open reading frame including transcribed 5' and 3' flanking sequences. Alternatively, it may comprise an anti-sense sequence in that it encodes the complement of an RNA molecule or portion thereof. When the construct includes an open reading frame (ORF) which encodes a protein, an enhanced transcription initiation rate is obtained, usually providing an increased amount of the polypeptide expression product of the gene. When the construct comprises an anti-sense sequence, the enhanced transcription of RNA complementary to wild type suppresses the expression of the wild type mRNA, thereby decreasing the amount of the polypeptide expression product. In addition, antisense RNA can also function as an inhibitor of replication of RNA (of vital genomes for example).

Enhanced transcription in plants may find use in enhancing the production of proteins characteristic of the plant (endogenous) or those proteins from other genetic sources (exogenous). (By endogenous is intended normally found in the wild-type host, while exogenous intends not normally found in the wild-type host.)

The initiation regions of the subject invention may be used in a variety of contexts and in combination with a variety of sequences, "RNA coded sequences." The RNA coded sequences of a gene may be those of a natural gene, including the open reading frame for protein coding and frequently the 5' and 3' untranslated sequences. The RNA translational initiation sequences are included in the constructs, either from the promoter domain or from the attached coding sequences.

The RNA coded sequence will include:

1. Protein encoding sequences of a gene (plant, animal, bacterial, vital, and fungal) which may be employed include: (a) natural open reading frame encoding a protein product; (b) complementary DNA (cDNA) sequences derived from mRNA of a gene; (c) synthetic DNA giving the appropriate coding sequence; (d) protein encoding sequences derived from exons of the natural gene, i.e., open reading frame produced by exon ligation; (e) combinations thereof.

Attached to the above sequences are appropriate transcription termination/polyadenylation sequences.

2. Sequences from the natural gene (plant, animal, bacterial, vital, and fungal) which encode the primary RNA product, i.e., consisting of exons and introns, e.g., natural Polymersac II and Polymerase III transcribed genes of eukaryotes.

3. Synthetic DNA sequences which encode a specific RNA or protein product.

4. Sequences of DNA modified from known (natural gene) coding sequences by mutagenesis, for example, site specific mutagenesis.

5. Chimeras of any of the above achieved by ligation of DNA fragments, e.g., which encode fused proteins.

6. DNA sequences encoding the complement of RNA molecules or portions thereof.

Examples of the above sequences to be expressed from the promoter-enhancer constructs of the subject invention include: antisense RNAs (for gene suppression); nutritionally important proteins; growth promoting factors; proteins giving protection to the plant under certain environmental conditions, e.g., proteins giving resistance to metal or other toxicity; stress related proteins giving tolerance to extremes of temperature, freezing, etc.; compounds of medical importance, e.g., antimicrobial, anti-tumor, etc.; proteins of specific commercial value; increased level of proteins, e.g., enzymes of metabolic pathways, increased levels of products of structural value to a plant host, e.g., herbicide resistance, such as increased amounts of EPSP synthase (Shah et al., *Science* (1986) 233:417) , pesticide resistance, e.g., B. thuringiensis toxin, etc. The sequences of interest which are transcribed will be of at least about 8 bp, usually at least about 12 bp, more usually at least about 20 bp, and may be one or more kbp.

In some instances it will be desirable to delete the untranslated upstream region of the gene at a site fewer than 250 bp ($-250$) from the initiation codon ($+1$), usually fewer than 150 bp, more usually fewer than 100 bp, but not less than about 50 bp, more usually not less than about 70 bp. Truncation will be of particular interest where an inverted repeat of a total of at least 8 bp, usually at least 10 bp is present in the region. Usually, the truncation will be upstream from the CAAT box of the upstream promoter region.

Conveniently the DNA construct can additionally include a selection marker. Exemplary of markers useful in plant cells are bleomycin, hygromycin, kanamycin resistance, e.g. neomycin Phosphotransferase type II gene (which permits selective growth of transformed plant tissue in the presence of kanamycin or G418), and glucuronidase. Exemplary of such markers useful in animal cells are thymidine kinase, dihydrofolate reductase, those identified above, etc.

The subject constructs will be prepared employing cloning vectors, where the sequences may be naturally occurring, mutated sequences, synthetic sequences, or combinations thereof. The cloning vectors are well known and comprise prokaryotic replication systems, markers for selection of transformed host cells, and unique dual restriction sites for insertion or substitution of sequences. For transcription and optimal expression, base DNA may be transformed into a host, e.g. mammalian host, for integration into the genome, where the subject construct is Joined to a marker for selection or is co-transformed with DNA encoding a marker for selection. Alternatively, episomal elements (plasmids) may be employed which may be introduced into the host cell by transformation, transfection, transduction, conjugation, electroporation, fusion, etc. where the episomal element may be stably maintained at a copy number of 1 or greater or may be integrated into the host cell genome.

The manner in which the subject constructs are introduced into the host cell is not critical to this invention. Nor is it critical that the construct be an extrachromosomal element or integrated into the host genome. With plants the construct may be introduced using *A. tumefaciens* using a T-DNA construct with left and right borders, electroporation, microinjection, etc. With mammalian cells, transformation or transfection may be employed.

In a particular embodiment of the invention, the enhancer domain comprises a modified CaMV 35S enhancer with a heterologous promoter or 35S promoter or an unmodified 35S enhancer with a heterologous promoter. Desirably, an enhancer domain is employed having at least one more repetitive unit than the natural CaMV 35S enhancer, desirably having two 35S enhancer domains in tandem in either orientation. Illustrative of heterologous promoters are Ti-plasmid promoters, such as the T-DNA gene 5 and 7 promoters.

The constructs may be used with cells in suspension culture, tissue, organisms, e.g. plants, callus, or the like.

A variant of the CaMV 35S enhancer promoter in which the sequences upstream of the TATA element were tandemly duplicated was constructed. Transcription from the 35S promoter in transgenic plants was increased ten-fold by this modification. The duplicated upstream region of the CaMV 35S promoter also acted as a strong transcriptional enhancer of heterologous promoters, increasing the transcription rate of an adjacent and divergently transcribed T-DNA gene, i.e., gene 7, several hundredfold and, to a lesser extent, that of another T-DNA gene from a remote downstream position. This engineered enhancer element increased the expression of foreign genes in transgenic plant cells and plants.

The following examples are offered by way of illustration and not by way of limitation.

EXPERIMENTAL

The efficiency of transcription of the natural CaMV 35S promoter was raised by duplicating the transcription-activating sequences upstream of the TATA element, as shown in FIG. 1. The natural and duplicated 35S promoters were transferred to tobacco plants for functional analysis by the use of intermediate vectors derived from pMON178. Preparation of those vectors is described in detail, below. Briefly, pMON178 is a modification of pMON129 (Fraley et al., *Proc. Natl. Acad. Sci. USA* (1983) 80:4803–4807) containing a nopaline synthase (NOS) gene, a chimaeric neomycin Phosphotransferase type II (NPT) gene which permits selective growth of transformed plant tissue in the presence of kanamycin, and an 1800 bp fragment from the transferable region (T-DNA) of an octopine-type Ti plasmid (FIG. 1). The NPT-encoding sequences of pMON178 are linked to a promoter that was derived from the NOS gene. This promoter was excised and replaced by 35S promoters with single or double copies of the upstream region to make the intermediate vectors pCKR1 or pCKR2 (FIG. 1).

The CaMV 35S sequences are from the CAbb BS strain, as reported by Franck et al., *Cell* (1980) 21:285–294.

Structures of Genes in Intermediate Vectors and in Transgenic Plants

Vectors were prepared as illustrated in FIG. 1. Abbreviations used in the Figure are B, BamHI; EV, EcoRV; H, HindIII; P, PstI; (EV/P), fusion of EcoRV and PstI sites. A fragment of the 35S promoter extending between positions −343 to +9 was previously constructed in pUC13 by Odell et al., supra. It was excised as a ClaI-HindIII fragment, made blunt-ended with DNA polymerase I (Klenow fragment), and inserted into the HincII site of pUC18 to make pCA1. The upstream region of the 35S promoter was excised from this plasmid as a HindIII-EcoRV fragment and inserted into pCA1 between the HindIII and PstI (blunt) sites to make pCA2. The unrearranged or duplicated 35S promoters were excised from pCA1 or pCA2, respectively, as HindIII-BamHI fragments and inserted between the HindIII and BglII sites of pMON178 to make the intermediate vectors pCKR1 or pCKR2.

Intermediate vectors were transferred from E coli to A tumefaciens by triparental mating Those that had integrated into resident Ti plasmids by recombination were selected as described (Rogers et al., *Methods in Enzymol.* (1986) 118:627–640). The recombination event resulted in linkage of the intermediate vector sequences to Ti plasmid sequences including the left T-DNA border and a complete promoter for gene 5. (See Willmitzer et al., *EMBO J.* (1982) 1:139–146). After infection of leaf discs, the DNA between the right (RB) and the left (LB) border sequences of the recombinant Ti plasmid was transferred to and chromosomally integrated into the plant cells, with the transferred genes arranged as shown at the bottom of FIG. 1. The open boxes represent promoters and arrows represent transcribed regions.

The intermediate vectors were established in *A. tumefaciens* by homologous recombination with resident copies of the disarmed octopine-type Ti plasmid pTiB6S3SE as described previously (Rogers et al. (1986) supra). The recombinant plasmids contained the octopine-type T-DNA genes 5 and 7 (Willmitzer et al. (1982) supra) (structural details of T-DNA gene 7, including the complete DNA sequence are described in McPherson, *Nuc. Acids Res.* (1984) 12:2317–2325 ) and the NPT and NOS genes of the intermediate vector, all of which are flanked by right and left T-DNA border sequences which delineated the region of the Ti plasmid that was integrated into the genome of transformed plant cells.

Leaf discs of *Nicotiana tabacum* cv. xanthi H38 were infected with cultures of recombinant *A. tumefaciens* and cultured in vitro as described (Rogers et al. (1986) supra). Tobacco cells carrying stably integrated copies of the NPT gene and associated DNA were selected by growth of calli and subsequent shoot development in the presence of 300 μg/ml of kanamycin. Individual shootlets were excised from the transformed tissue and grown to a height of 40 to 60 cm. Analysis of DNA isolated from leaves showed that one to five intact copies of each of the four transferred genes were present in the genomes of the regenerated plants.

NPT and T-DNA Gene 7 Transcripts in Transgenic Plants (Throughout the text gene 7 and gene 5 refer to the T-DNA genes. See McPherson, *Nucleic Acids Res.* (1984) 12:2317-2325.)

The amounts and initiation sites of transcripts of the transferred genes were determined by their protection of single-stranded DNA probes from digestion by S1 nuclease.

To determine the amount of transcription, leaves were ground in a mortar in 25 mM EDTA pH 7.5, 75 mM NaCl, 1% SDS, and extracted twice with phenol and once with isobutanol. Liberated nucleic acids were precipitated by the addition of 0.1 volume of 3 M sodium acetate pH 5.5 and 2 volumes of ethanol. RNA was recovered from the nucleic acid samples by precipitation with LiCl as described (McPherson et al., *Proc. Natl. Acad. Sci. USA* (1980) 77:2666-2670). Single-stranded continuously labelled DNA probes were synthesized, hybridized with 2 μg of leaf RNA, digested with S1 nuclease, and analysed by electrophoresis as described (Kay et al. (1986) *Mol. Cell Biol.* 6: 3134-31.

The 35S/NPT probe was synthesized from an M13mp18 template containing an insert of the HindIII-PvuII fragment of the 35S/NPT gene isolated from pCKR1, and was excised from template DNA by digestion with EcoRV. The gene 7 probe was synthesized from an M13mp18 template containing the HindIII-PvuII fragment of gene 7 isolated from the HindIII Y fragment of the octopine Ti plasmid pTiB6 806 (Gelvin et al., *Proc. Natl. Acad. Sci. USA* (1982) 79:76-80), and was excised by digestion with HindIII.

Transcripts in total leaf RNA were identified and quantified by S1 nuclease protection. The four plants of each transformed type are a representative selection of the six to ten plants of each type that were examined for gene expression. Equivalent levels of transcriptional activation by the unrearranged and duplicated 35S promoters were observed in additional sets of plants derived from independent transformation experiments. When linked to a NOS promoter (pMON178), the NPT-encoding sequences were transcribed at low levels in the leaves of transgenic plants.

Replacement of the NOS promoter by a wild-type CaMV 35S promoter (CKR1) resulted in a ten-fold increase on average in the number of NPT transcripts. However, the modified 35S promoter with a duplicated upstream region (CKR2) had by far the highest activity, producing roughly one hundred times as many NPT transcripts as did the NOS promoter.

The promoter of the chimaeric NPT gene was positioned immediately upstream of the divergently transcribed gene 7 in the transgenic plants (FIG. 1). With a NOS promoter linked to the NPT-encoding sequences, gene 7 was transcribed at barely detectable levels, as described above. Gene 7 transcription was increased about forty-fold above these levels by the presence of an upstream and divergently oriented 35S enhancer/promoter. A further ten-fold increase in gene 7 transcription was induced when the upstream region of the NPT-linked 35S enhancer region was duplicated. In this situation the enhancer sequence (the upstream region of the 35S promoter) served as a bidirectional promoter-activating element.

The proportions of NPT and gene 7 transcripts were not the same among different plants that had been transformed with the same DNA, even when these two genes were being simultaneously activated by the 35S upstream region (enhancer sequence). Variability in rates of transcription among either closely linked or widely separated genes within the same fragment of transferred DNA is commonly observed in transgenic plants (Jones et al., *EMBO J.* (1985) 4:2411-2418, Nagy et al., *EMBO J.* (1985) 4:3063-3068, and Velten et al., *Nucleic Acids Res.* (1985) 13:6981-6998); the causes of such variation in gene expression are unknown.

In addition to activating transcription of the proximal 35S and gene 7 promoter elements, the duplicated upstream region of the 35S promoter was able to greatly increase transcription at a pair of initiation sites in the gene 5 promoter, despite being located about 2000 bp downstream of it, as described below.

Gene 5 Transcripts in Transgenic Plants

Transcripts in 2 μg of leaf RNA were identified and quantified by S1 nuclease protection of probes as described previously. Two classes of Gene 5 transcripts were identified, initiating about 320 bases (+1) and 300 bases (+20) upstream of the RsaI site. The probe was synthesized from an M13mp18 template containing an insert of the HindIII-RsaI fragment of gene 5 isolated from the HindIII Y fragment of the octopine Ti plasmid pTiB6 806 (Gelvin et al., *Proc. Natl. Acad. Sci. USA* (1982) 79:76-80), and was excised at the SstI site in the M13mp18 polylinker beyond the insert.

The remote activation of the gene 5 promoter identifies the upstream region of the 35S promoter as a true transcriptional enhancer (Khoury et al., *Cell* (1983) 33:313-314, and Shaffner, *Eukaryotic Transcription: the Role of cis-and trans-acting Elements in Initiation* (1985) ed. Y. Gluzman, 1-18).

The transcript levels of gene 5 were much lower than those of gene 7 when both were being activated by the duplicated 35S enhancer. This reflects the natural difference in the strengths of their promoters (Willmitzer et al. (1982) supra and Gelvin et al. (1982) supra) but the greater distance between the enhancer and the gene 5 promoter could also result in a lesser degree of transcriptional activation, as observed with other enhancers (Wasylyk et al., *Nucleic Acid Res.* (1984) 12:5589-5608).

Transcription of the NOS gene was not significantly affected by the presence of a duplicated 35S enhancer at a remote and downstream location on the same fragment of transferred DNA, as described below.

NOS Gene Transcripts in Transgenic Plants

Transcripts in 2 μg of leaf RNA were identified and quantified by S1 nuclease protection of probes as described previously. The probe was synthesized from an M13mp19 template containing an insert of the EcoRI-HpaII fragment of the NOS gene isolated from pMON178, and was excised by digestion with NdeI.

Construction of Other Vectors

The following exemplary DNA constructs comprising transcription initiation regions of the present invention were prepared.

Figure 2:
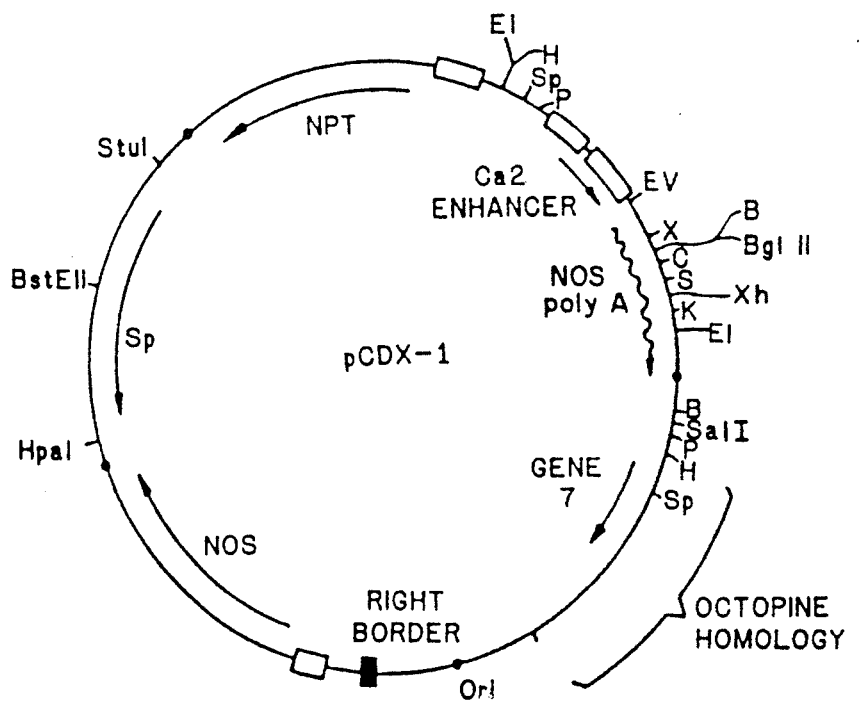
FIG. 2 is a diagrammatic structure of pCDX-1.

A modified version of pMON31 6 (Rogers et al., *Biotechnology in Plant Sciences: Relevance to Agriculture in the Nineteen Eighties* (1986) Academic Press 219), called pCDX1, which has duplicated 35S enhancer sequences upstream of a polylinker insertion site and a polyadenylation signal sequence was constructed as illustrated in FIG. 2.

Construction of pCDX1

The duplicated 35S enhancer domain was excised from pCA2 as a HindIII-BamH1 fragment and ligated to the BglII - BstEII fragment of pMON 316 (containing the T-DNA right border) and the BstEII - Eco RI fragment of pMON 200 (containing the Nos-NPT gene). The EcoRI and HindIII sites were made blunt ended with DNA polymerase 1 (Klenow fragment) and ligated together to give the final plasmid, pCDX1.

Promoter-enhancer Constructs Combining the Enhancer Sequences of CaMV 35S and the Promoter of T-DNA Gene 7A A. Construction of Regions CE7 and CD7 in Plasmids pCE7 and pCD7

The MnlI (270 bp) fragment containing upstream sequences and the promoter of T-DNA gene 7 was excised from T-DNA cloned sequences. The MnlI fragment was inserted into the SmaI site of pUC 18 to give pC7.

Figure 3A:
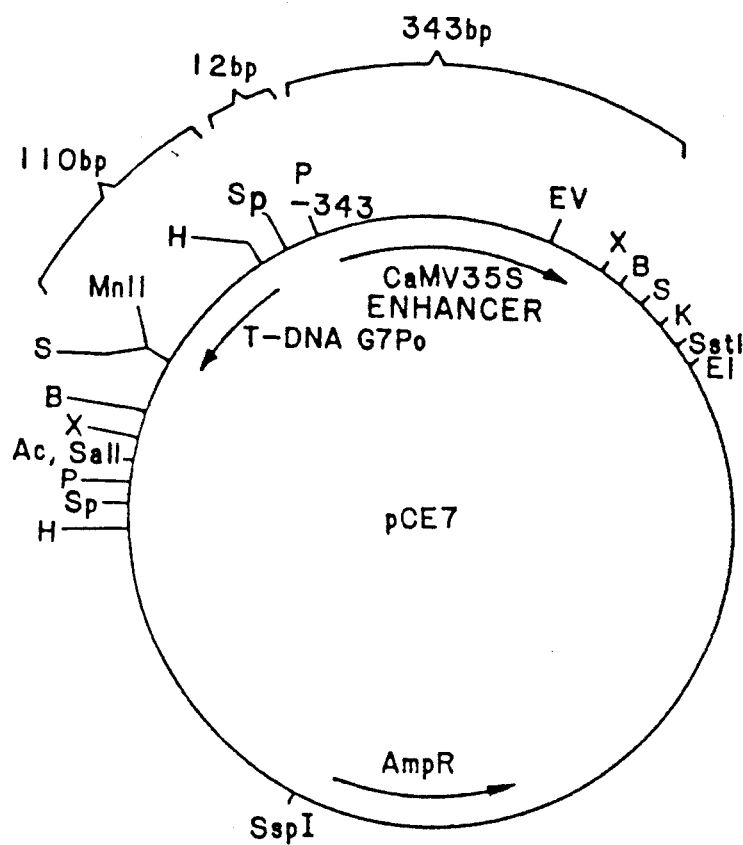
FIG. 3A is a diagrammatic structure of pCE7.
Figure 3B:
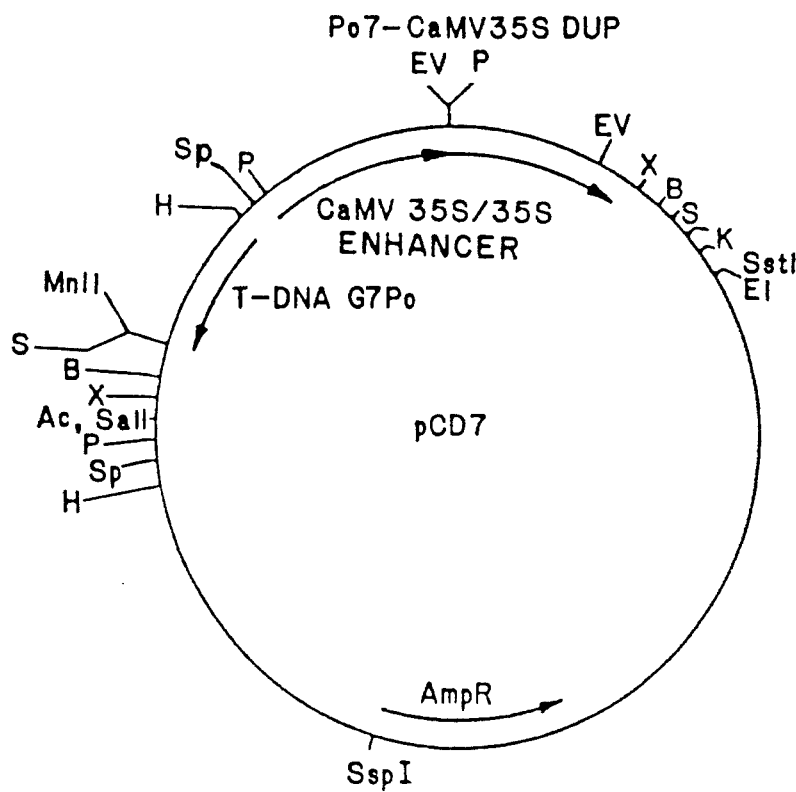
FIG. 3B is a diagrammatic structure of pCD7.

The HindIII fragment of pC7 containing the promoter region of T-DNA gene 7 and adjacent polylinker was excised and inserted:

1. into the HindIII site upstream of the CaMV 35S enhancer region in pCa1 to align the T-DNA gene 7 promoter with the adjacent natural CaMV 35S enhancer domain producing a "region", CE7 of plasmid pCE7 (FIG. 3A).
2. into the HindIII site upstream of the duplicated CaMV 35S sequences in pCa2 to align the T-DNA gene 7 promoter with the adjacent duplicated CaMV 35S enhancer domain producing a "region" CD7 of plasmid pCD7 (FIG. 3B).

Figure 4A:
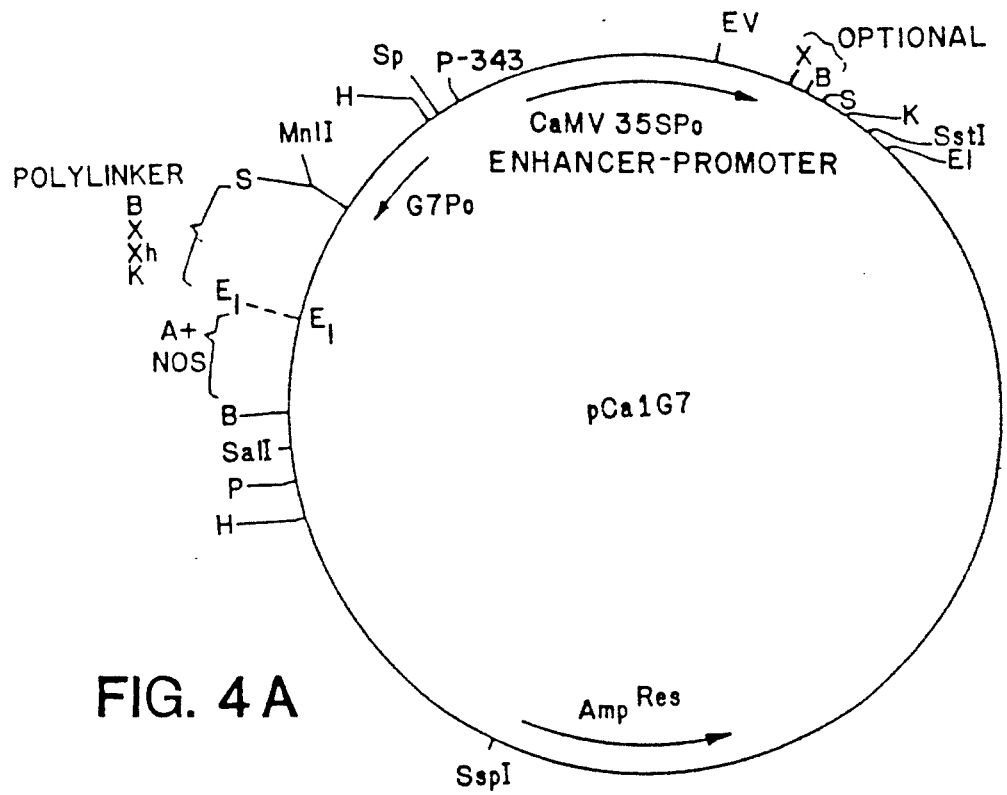
FIG. 4A is a diagrammatic structure of pCa1G7.
Figure 4B:
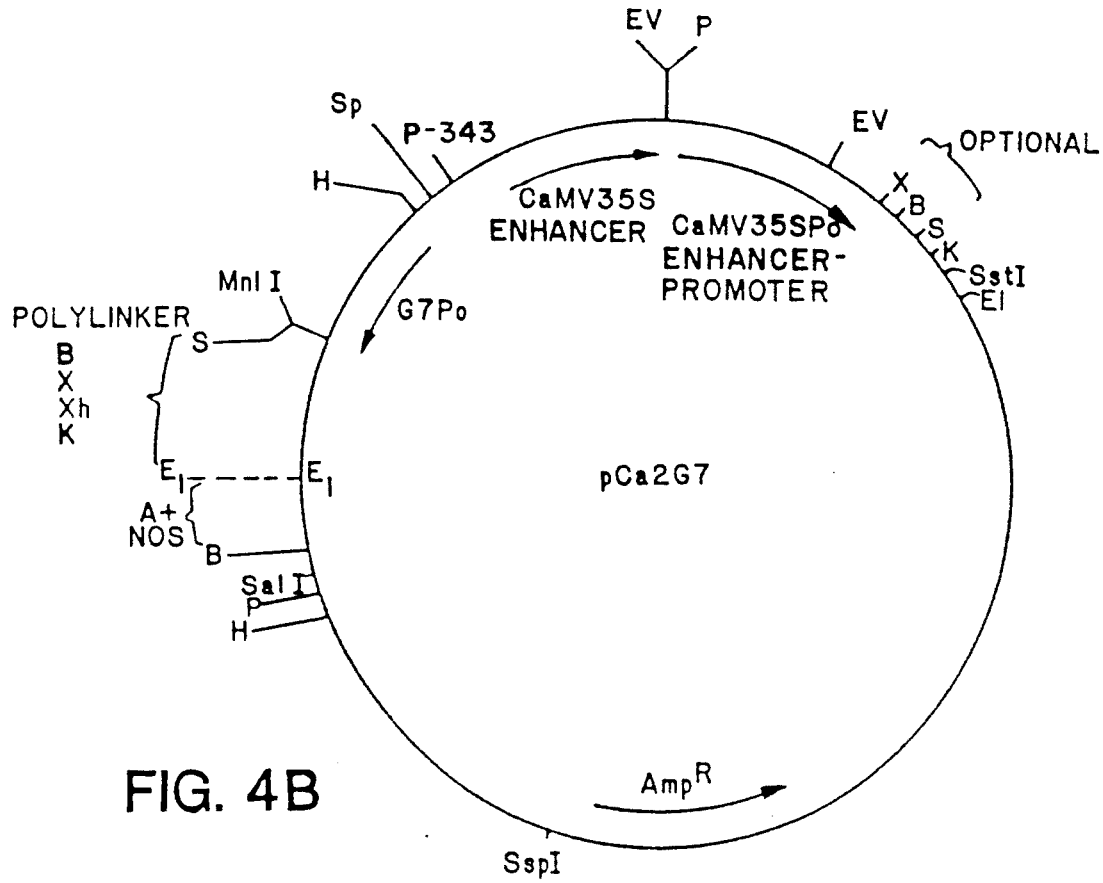
FIG. 4B is a diagrammatic structure of pCa2G7.
Figure 5:
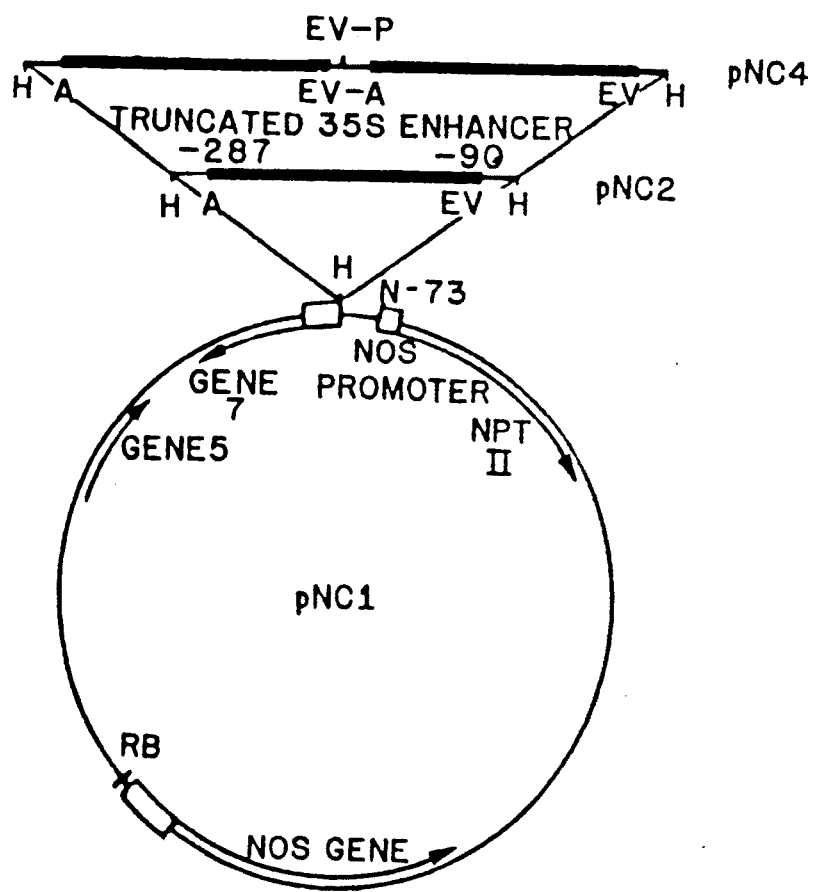
FIG. 5 is a diagrammatic structure of pNC1 with the inserts for pNC2 and pNC4.

The enhancer-promoter regions CE7 and CD7 are also marked in FIGS. 4A and 4B.

B. Plasmids pCa1G7 and pCa2G7

These plasmids facilitate the attachment of the regions CE7 and CD7 to gene coding sequences (including termination sequences) via polylinkers.

pCa1G7 (FIG. 4A) and pCa2G7 (FIG. 4B) are constructed by intially making a co-integrate plasmid by ligating together the following fragments:

the BstEII - EcoRI fragment of pMON 200;
the EcoRI-AccI fragment of pC7;
and the ClaI - BstEII fragment of pMON 316.

The HindIII fragment of this plasmid, carrying the gene 7 promoter (i.e., HindIII - MnlI) and adjacent polylinker is excised and ligated into:

1. the HindIII site of pCa1 (to give pCa1G7);
2. the HindIII site of pCa2 (to give pCa2G7).

These intermediate vectors are useful for obtaining efficient expression of protein-encoding sequences in transgenic plants. The vector pCKR2 can be used for the same purpose if a complete transcription unit is inserted at the HindIII site of the vector with its promoter adjacent to the 35S enhancer elements.

The extent of activation of a promoter by an enhancer appears to differ for different promoters.

Of the three heterologous promoters that were examined, the NOS promoter was not as highly activated by the 35S enhancer. Therefore, promoter domains may be screened for their responsiveness to a particular enhancer.

In the following examples, pNC1 was constructed by replacing the EcoRI-HindIII NOS/NPTII fragment of pMON178 with the EcoRI-HindIII NOS/NPT fragment of pNNSΔNC. pNNSΔNC was obtained from pNNS which resulted from the insertion of the HpaI-HindIII fragment of pMON129 into the SmaI-HindIII sites of pUC18. By deleting the upstream region −73 to −256 of the NOS promoter by digestion with NheI and ClaI and filling in with the Klenow fragment followed by ligation, pNNSΔNC was obtained.

pNC2, −3 and −4 were constructed by inserting the CaMV HindIII fragment of the pAV-H series (H1A, H1B and H2, respectively) into the HindIII site of pNC1. pAV-H plasmids have AluI to EcoRV sequences of the CaMV 35S enhancer inserted into the HincII sites of pUC1813 (Kay and McPherson, *Nucleic Acids Res.* (1987) 15:2778. pAV-H1 A and -H1B have a single insert in the (+) or (−) orientation, while pAV-H2 has a double insert with both AluI-EcoRV copies in the same orientation. (See FIG. 5.)

Alternative transcription initiation regions for enhanced expression from the T-DNA gene 7 promoter and from the NOS initiation region (i.e. truncated promoter to −73) are represented in the constructs pNC2 and pNC4. The single upstream region of the CaMV 35S enhancer comprises 8 of the 10 GTGG or (CCAC) repeats previously associated with the CaMV 35S upstream region. Is also includes the three extended repeats $$\text{GTGG}^{AAA}_{TTT},$$

i.e. at sites −100, −140, and −260. The duplicate of this region is represented in pNC4.

Levels of enhanced transcription from the T-DNA gene 7 promoter are higher for the single construct than in CKR1. For expression levels of gene 7, the duplicated form of the truncated 35S upstream region is equivalent to the duplicated form in CKR2.

The expression level from the truncated NOS promoter in the absence of the 35S upstream sequence (i.e. pNC1 ) was undetectable. In the presence of a single (pNC2 or 3) or double (pNC4) copy of the EcoRV-AluI region of the CaMV 35S upstream region, the enhancement of expression from the NOS initiation site was greater than that obtained with an intact NOS promoter region, i.e. −258 to +1. These results support the conclusion that sequences between −73 and −258 of the NOS upstream region have an inhibitory or regulatory effect on the CaMV 35S enhancer.

In accordance with the subject invention, novel DNA constructs are provided which allow for increased rate of transcription initiation of varying degrees. Thus, employing the same promoter region, various levels of transcription initiation are achieved in the absence of an enhancer or the presence of a wild-type enhancer or extended enhancer. These constructions can have wide application in the control of the formation of expression products, protection against pathogens or antibiotics, etc.

Although the foregoing invention has been described in some detail by way of illustration and example for purposes of clarity of understanding, it will be obvious that certain changes and modifications may be practiced within the scope of the appended claims.

What is claimed:

1. A chimeric transcriptional initiation region comprising:

as operably joined components (i) a tandemly duplicated CaMV 35S enhancer sequence comprising an AluI-EcoRV fragment of a CaMV 35S upstream region; and (ii) a promoter comprising an RNA polymerase binding site and an mRNA initiation site, wherein when a nucleotide sequence of interest is transcribed under the regulatory control of said chimeric transcriptional initiation region, the amount of transcription product is enhanced as compared to the amount of transcription obtained with a chimeric transcriptional initiation region comprising a single copy of said CaMV enhancer sequence and said promoter.

2. The chimeric transcriptional initiation region according to claim 1, wherein said promoter is obtainable from the upstream region of a plant virus gene.

3. The chimeric transcriptional initiation region according to claim 2, wherein said plant virus gene is a CaMV 35S gene.

4. The chimeric transcriptional initiation region according to claim 1, wherein said promoter is obtainable from the upstream region of a gene indigenous to a plant cell genome.

5. The chimeric transcriptional initiation region according to claim 1, wherein said promoter is a T-DNA promoter.

6. The chimeric transcriptional initiation region according to claim 5, wherein said promoter is a T-DAN gene 7 or gene 5 promoter.

* * * * *

US005322938C1

(12) EX PARTE REEXAMINATION CERTIFICATE (6221st)
United States Patent
McPherson et al.

(10) Number: US 5,322,938 C1
(45) Certificate Issued: May 6, 2008

(54) DNA SEQUENCE FOR ENHANCING THE EFFICIENCY OF TRANSCRIPTION

(75) Inventors: Joan C. McPherson, Vancouver (CA); Robert Kay, West Vancouver (CA)

(73) Assignee: Monsanto Technology LLC, St. Louis, MO (US)

Reexamination Request:
No. 90/008,249, Sep. 29, 2006

Reexamination Certificate for:
Patent No.: 5,322,938
Issued: Jun. 21, 1994
Appl. No.: 07/977,600
Filed: Nov. 17, 1992

Related U.S. Application Data

(63) Continuation of application No. 07/395,155, filed on Aug. 17, 1989, now Pat. No. 5,164,316, which is a continuation of application No. 07/147,887, filed on Jan. 25, 1988, now abandoned, which is a continuation-in-part of application No. 07/002,780, filed on Jan. 13, 1987, now abandoned.

(51) Int. Cl.
C12N 15/82 (2006.01)
C07H 21/04 (2006.01)

(52) U.S. Cl. .................... 536/24.1; 435/69.1; 435/70.1; 435/320.1

(58) Field of Classification Search .................. None
See application file for complete search history.

(56) References Cited

U.S. PATENT DOCUMENTS

| | | |
|---|---|---|
| 4,407,956 A | 10/1983 | Howell |
| 4,536,475 A | 8/1985 | Anderson |
| 5,352,605 A | 10/1994 | Fraley et al. |

FOREIGN PATENT DOCUMENTS

| | | |
|---|---|---|
| EP | 0 131 623 B2 | 7/1999 |
| WO | WO 84/02913 | 8/1984 |

OTHER PUBLICATIONS

Zenke et al., (EMBO J 5(2) : 387–397, 1986).*
Rogers et al (Methods in Enzymology, vol. 118: 627–640, 1986).*
Guilley et al., "Transcription of Cauliflower Mosaic Virus DNA: Detection of Promoter Sequences, and Characterization of Transcripts," *Cell*, 30(3): 763–773 (1982).
Boshart, Michael, et al., A very strong enhancer is located upstream of an immediate early gene of hyman cytomegalovirus, *Cell* 41:521–530 (1985).
Dennis, Elizabeth, et al., Transcription from a plant gene promoter in animal cells, *Nucleic Acids Research* 13(22):7945–7957 (1985).
Hunt, Arthur G., et al., Plant cells do not properly recognize animal gene polyadenylation signals, *Plant Molecular Biology* 8(1):23–35 (1987).
Kay, Robert, et al., Duplication of CaMV 35S promoter sequences creates a strong enhancer for plant genes, *Science* 236:1299–1302 (1987).

Khoury, G., et al., Enhancer elements, *Cell* 33:313–314 (1983).
Rogers, S.G., et al., Improved vectors for plant transformation: expression cassette vectors and new selectable markers, *Methods in Enzymology* 153:253–277 (1987).
Sanders, P.R., et al., Comparison of cauliflower mosaic virus 35S and nopaline synthase promoters in transgenic plants, *Nucleic Acids Research* 15(4):1543–1558 (1987).
Odell, Joan T., et al., Properties of an isolated transcription stimulating sequence derived from the cauliflower mosaic virus 35S promoter, *Plant Molecular Biology* 10(3):263–272 (1988).
Abel, Patricia Powell, et al., Delay of disease development in transgenic plants that express the tobacco mosaic virus coat protein gene, *Science* 232:738–743 (1986).
Barton, Kenneth A., et al., Regeneration of intact tobacco plants containing full length copies of genetically engineered T–DNA, and transmission of T–DNA to R1 progeny, *Cell* 32:1033–1043 (1983).
Bevan, Michael W., et al., Expression of tobacco mosaic virus coat protein by a cauliflower mosaic virus promoter in plants transformed by *Agrobacterium*, *The EMBO Journal* 4(8):1921–1926 (1985).
Caplan, A., et al., Introduction of genetic material into plant cells, *Science* 222:815–821 (1983).
Fraley, Robert T., et al., The SEV system: a new disarmed Ti plasmid vector system for plant transformation, *Bio/Technology* 3(7):629–635 (1985).
Morelli, Giorgio, et al., A short conserved sequence is involved in the light–inducibility of a gene encoding ribulose 1,5–biphosphate carboxylase small subunit of pea, *Nature* 315:200–204 (1985).
Nester, Eugene W., et al., Crown gall: a molecular and physiological analysis, *Annual Review of Plant Physiology* 35:387–413 (1984).
Shah, Dilip M., et al., Engineering herbicide tolerance in transgenic plants, *Science* 233:478–481 (1986).
Simpson, J., et al., Light–inducible and tissue–specific pea lhcp gene expression involves an upstream element combining enhancer– and silencer–like properties, *Nature* 323:551–554 (1986).
Zambryski, Patricia, et al., Ti plasmid vector for the introduction of DNA into plant cells without alteration of their normal regeneration capacity, *The EMBO Journal* 2(12):2143–2150 (1983).
Banerji, Julian, et al., Expression of a β–globin gene is enhanced by remote SV40 DNA sequences, *Cell* 27:299–308 (1981).
Chilton, Mary–Dell, et al., Tailoring the agrobacterium Ti plasmid as a vector for plant genetic engineering, *Stadler Symposium* 13:39–52 (1981).

(Continued)

*Primary Examiner*—Padmashri Ponnaluri

(57) ABSTRACT

Novel transcription initiation regions that provide for enhanced transcription or a DNA sequence, particularly a plant sequence, are provided.

OTHER PUBLICATIONS

Franck, A., et al., Nucleotide sequence of cauliflower mosaic virus DNA, *Cell* 21(1):285–294 (1980) [abstract only].

Gardner, Richard C., et al., "Plant viral vectors: CaMV as an experimental tool," *Genetic Engineering of Plants—An Agricultural Perspective* (Tsune Kosuge, et al., eds.), New York: Plenum Press, 1983, pp. 121–142 [presented at conference on genetic engineering of plants, University of California at Davis, Aug. 15–19, 1982].

Guilley, Hubert, et al., Transcription of cauliflower mosaic virus DNA: detection of promoter sequences, and characterization of transcripts, *Cell* 30(3):763–773 (1982).

Herrera–Estrella, Luis, et al., Chimeric genes as dominant selectable markers in plant cells, *The EMBO Journal* 2(6):987–995 (1983).

Howarth, Alan J., et al., Plant viruses with genomes of single–stranded DNA, *Trends In Biochemical Science* 7:180–182 (1982).

Hu, Nien–Tai, et al., Primary structure of a genomic zein sequence of maize, *The EMBO Journal* 1(11):1337–1342 (1982).

Hull, Roger, et al., Does cauliflower mosaic virus replicate by reverse transcription?, *Trends In Biochemical Science* 8(4):119–121 (1983).

Hull, Roger, et al., Replication of cauliflower mosaic virus DNA, *Science Progress, Oxford* 68:403–422 (1983).

Maliga, P., et al., Streptomycin resistant plants from callus culture of haploid tobacco, *Nature New Biology* 224:29–30 (1973).

McKnight, T.D. and T.B. Meagher, Isolation and mapping of small cauliflower mosaic virus DNA fragments active as promoters in *Escherichia–coli, Journal of Virology* 37(2):673–682 (1981) [abstract only].

Messing, Joachim, et al., "Plant gene structure," *Genetic Engineering of Plants—An Agricultural Perspective* (Tsune Kosuge, et al., eds.), New York: Plenum Press, 1983, pp. 211–227 [presented at conference on genetic engineering of plants, University of California at Davis, Aug. 15–19, 1982].

Mulligan, Richard C., et al., Expression of a bacterial gene in mammalian cells, *Science* 209:1422–1427 (1980).

Pfeiffer, Pierre, et al., Involvement of reverse transcription in the replication of cauliflower mosaic virus: a detailed model and test of some aspects, *Cell* 33:781–789 (1983).

Shah, Dilip M., et al., Complete nucleotide sequence of a soybean actin gene, *Proceedings of the National Academy of Sciences* 79(4):1022–1026 (1982).

Shannon, K.P., et al., Detection of aminoglycoside–modifying strains of bacteria, *Antibiotics* 183–198 (1983).

Sieg, K., et al., "Introduction and propagation of foreign DNA in plants using cauliflower mosaic virus as vector," in *NATO Advanced Studies Institute/Federation of European Biological Societies Advanced Course: Structure and Function of Plant Genomes*, Porto Portese, Italy, Aug. 23, 1982–Sep. 2, 1982, p. 154 [abstract].

Stanley, John, et al., Nucleotide sequence of cassavata latent virus DNA, *Nature* 301:260–262 (1983).

Wigler, Michael, et al., Transfer of purified herpes virus thymidine kinase gene to culture mouse cells, *Cell* 11:223–232 (1977).

Condit, Carol M., et al., "Multiple viral specific transcripts from the genome of cauliflower mosaic virus," presented at *Advances in Gene Technology: Molecular Genetics of Plants and Animals*, The Fifteenth Miami Winter Symposium, Jan. 17–21, 1983 (F. Ahmad, et al., eds.) (1983), p. 564 [abstract].

de Framond, Annick J., et al., "Mini–Ti plasmid and a chimeric gene construct: new approaches to plant gene vector construction," presented at *Advances in Gene Technology: Molecular Genetics of Plants and Animals*, The Fifteenth Miami Winter Symposium, Jan. 17–21, 1983 (F. Ahmad, et al., eds.), Academic Press, 1983, pp. 159–170.

Fraley, R.T., et al., "Use of a chimeric gene to confer antibiotic resistance to plant cells," presented at *Advances in Gene Technology: Molecular Genetics of Plants and Animal*, The Fifteenth Miami Winter Symposium, Jan. 17–21, 1983 (F. Ahmad, et al., eds.), Academic Press, 1983, pp. 211–221; & *Chemical Abstracts* 101:149 (1984), ref. No. 205249p [abstract].

Gronenborn, Bruno, et al., Propagation of foreign DNA in plants using cauliflower mosaic virus as vector, *Nature* 294:773–776 (1981).

Herrera–Estrella, Luis, et al., Expression of chimaeric genes transferred into plant cells using a Ti–plasmid–derived vector, *Nature* 303:209–213 (1983).

Hohn, Thomas, et al., "Cauliflower mosaic virus on its way to becoming a useful plant vector," *Current Topics in Microbiology and Immunology*, vol. 96 (W. Henle, et al, eds.), Berlin, Germany: Springer–Verlag, 1982, pp. 193–236.

Kemp, John D., et al., "Agrobacterium–mediated transfer of foreign genes into plants," *Genetic Engineering: Applications to Agriculture* (Beltsville Symposium 7—Lowell D. Owen, ed.), Totowa, New Jersey: Rowman & Allanheld, 1983, pp. 215–228 [presented at *Genetic Engineering: Applications to Agriculture Symposium*, Beltsville, Maryland, May 16–19, 1982].

Marx, Jean L., Ti plasmids as gene carriers—when suitably modified, tumor–inducing plasmids can transfer genes into plant cells from which normal plants may be regenerated, *Science* 216:1305 (1982).

Schell, J., et al., "Gene vectors for higher plants," in *Genetic Engineering: Applications to Agriculture* (Beltsville Symposium 7—Lowell D. Owen, ed.), Totowa, New Jersey: Rowman & Allanheld, 1983, pp. 197–213.

Schell, Josef, et al., The Ti plasmids as natural and as practical gene vectors for plants, *Bio/Technology* 1:175–180 (1983).

Declaration of Joachim Messing dated Mar. 19, 1996 [attached to the Mar. 29, 1996 response filed in the opposition appeal proceedings of Publication No. 0 131 623, Case No. T 0387/94–3.3.4, with the Boards of Appeal for the European Patent Office].

Bevan, Michael W., Binary Agrobacterium vectors for plant transformation, Nucleic Acids Research 12(22):8711 8721 (1984).

Bryne, Barry J., et al., Definition of the simian virus 40 early promoter region and demonstration of a host range bias in the enhancement effect of the simian virus 40 72–base–pair repeat, *Proceedings of the National Academy of Sciences* 80(3):721–725 (1983).

Cullen, Byran R., et al., Transcriptional activity of avian retroviral long terminal repeats directly correlates with enhancer activity, *Journal of Virology* 53(2):515–521 (1985).

Horth, Marie, et al., Cloning of a *Nicotiana plumbaginifolia* protoplast–specific enhancer–like sequence, *The EMBO Journal* 6(9):2525–2530 (1987).

Lang, James C., et al., Transcriptional regulation of a herpes simplex virus immediate early gene is mediated through an enhancer–type sequence, *The EMBO Journal* 3(2):389–395 (1984).

Moreau, P., et al., The SV40 72 base repair repeat has a striking effect on gene expression both in SV40 and other chimeric recombinants, *Nucleic Acids Research* 9(22):6047–6068 (1981).

Ow, David W., et al., Functional regions of the cauliflower mosaic virus 35S RNA promoter determined by use of the firefly luciferase gene as a reporter of promoter activity, *Proceedings of the National Academy of Sciences* 84(14):4870–4874 (1987).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5 is confirmed.

Claim 6 is determined to be patentable as amended.

6. The chimeric transcriptional initiation region according to claim 5, wherein said promoter is a [T-DAN] *T-DNA* gene 7 or gene 5 promoter.

\* \* \* \* \*